United States Patent [19]

Scott et al.

[11] Patent Number: 5,112,608
[45] Date of Patent: May 12, 1992

[54] USE OF PROTEASE NEXIN-I TO MEDIATE WOUND HEALING

[75] Inventors: Randy W. Scott, Sunnyvale, Calif.; Richard A. Berg, Lambertville, N.J.

[73] Assignee: Incyte Pharmaceuticals, Redwood City, Calif.

[21] Appl. No.: 505,442

[22] Filed: Apr. 5, 1990

Related U.S. Application Data

[63] Continuation-in-part of Ser. No. 25,450, Mar. 13, 1987, which is a continuation-in-part of Ser. No. 871,501, Jun. 6, 1986, abandoned, which is a continuation-in-part of Ser. No. 870,232, Jun. 3, 1986, abandoned.

[51] Int. Cl.$^5$ .......................................... A61K 37/547
[52] U.S. Cl. ................................................ 424/94.64
[58] Field of Search ................ 424/94.1, 94.64, 94.63, 424/94.6, 443

[56] References Cited

U.S. PATENT DOCUMENTS

| | | | |
|---|---|---|---|
| 4,265,233 | 5/1981 | Sugitachi et al. | 128/155 |
| 4,904,469 | 2/1990 | Petereit et al. | 424/94.3 |
| 5,006,252 | 4/1991 | Scott et al. | 210/635 |

FOREIGN PATENT DOCUMENTS

0233838  8/1987  European Pat. Off. .

OTHER PUBLICATIONS

Meler et al., Letters to Nature, vol. 342 (1989), pp. 548–550.
Needels et al., Neuroscience, 18 (3) 1986, pp. 517–526.
Berg et al., J. Cell Biochem. Suppl., O (15 Part F) 1991 p. 192.
Gomez–Pinilla et al., Soc. Neurosci. Abstr., 16(2) 1990 p. 1346.
Rudge et al., J. of Neuroscience, 10 (11) 1990, pp. 3594–3603.
Ruppert et al., Matrix, 10(4) (1990) p. 246.
Scott et al., J. Biol Chem. (1985) 260(11):7029–7034.
Eaton et al., Chem. Abstracts (1984) 101(7):244 (abstract No. 50586v).
Gloor et al., Biol. Abstracts (1987) 83(7):792 (abstract No. 67719).
Erickson et al., Proc. Natl. Acad. Sci. (1985) 82:8710–8714.
Ny et al., Proc. Natl. Acad. Sci. (1986), 83:6776–6780.
Walsh, "Proteases in Biological Control" Reich et al., eds., (1975) Cold Spring Harbor Conferences on Cell Proliferation, vol. 2, New York, pp. 1–11.
Baker et al., Cell (1980) 21:37–45.
Low et al., Proc. Natl. Acad. Sci. (1981) 78(4):2340–2344.
Baker et al., The Receptors, vol. III (1985) Conn, P. M. ed., Academic Press, Chapter 5, pp. 153–172.
Scott et al., J. Biol. Chem. (1983) 258(17):10439–10444.
Guenther et al., EMBO Journal (1985) 4(8):1963–1966.
Barde et al., Nature (1978) 274:818.
Baker et al., J. Cell. Physiol. (1982) 112:291–297.
Low et al., Nature (1982) 298:476–478.
Lobb, Biochemistry (1988) 27(7):2572–2578.
Jones et al., Cancer Res. (1980) 40:3222–3227.
Bergman et al., Proc. Natl. Acad. Sci. (1986) 83:996–1000.
McGuire–Goldring et al., Arth. Rheum. (1984) 27:S24.
Monrad et al., Prog. Brain Res. (1983) 58:359–364.
Van Nostrand et al., Biochemistry (1988) 27:2176–2181.
McGrogan et al., Bio/Technology (1988) 6:172–177.

Primary Examiner—Douglas W. Robinson
Assistant Examiner—Susan M. Weber
Attorney, Agent, or Firm—Morrison & Foerster

[57] ABSTRACT

A method of treating wound healing with a composition containing protease nexin-I (PN-I) is disclosed. Compositions comprised of PN-I uniformly dispersed throughout a pharmaceutically acceptable carrier are disclosed as are such compositions further comprising antibiotics. Occlusive wound dressings are taught which are comprised of a support surface having an absorbent area thereon which has PN-I absorbed thereon and which absorbent area is surrounded by a pressure sensitive adhesive strip for adhering the dressing to a surface surrounding the wound to be treated.

15 Claims, 5 Drawing Sheets

FIG. 1-1

SEQUENCE OF PROTEASE NEXIN I TYPE ALPHA

```
CCG CTG TCT GCC ATC ATC CCA CAC ATC AGC ACC AAG ACC ATA GAC AGC ATC ATG GTG CCC AAG AGG ATG AGC ATC ATG GTG CAG GTG ATC CTG
Pro Leu Ser Ala Ile Ile Pro His Ile Ser Thr Lys Thr Ile Asp Ser Ile Met Val Pro Lys Arg Met Ser Trp Met Ser Ile Met Val Gln Val Ile Leu
                    250                             260                             270

CCC AAG TTC ACA GCT GTA GCA CAA ACA GAT TTG AAG GAG CCG CTG AAA GTT CTT GGC ATT ACT GAC ATG TTT GAT TCA TCA AAG GCA AAT
Pro Lys Phe Thr Ala Val Ala Gln Thr Asp Leu Lys Glu Pro Leu Lys Val Leu Gly Ile Thr Asp Met Phe Asp Ser Ser Lys Ala Asn
            280                             290                             300

TTT GCA AAA ATA ACA AGG TCA GAA AAC CTC CAT GTT TCT CAT ATC TTG CAA AAA ATT GAA GTC AGT GAA GAT GGA ACC AAA GCT
Phe Ala Lys Ile Thr Arg Ser Glu Asn Leu His Val Ser His Ile Leu Gln Lys Ile Glu Val Ser Glu Asp Gly Thr Lys Ala
    310                             320                             330       HindIII TCA GCA GCA ACA ACT GCA ATT CTC ATT GCA AGA TCA GAC AGA CCT TTT CTG TTT ATA GTA GAC CCT TTT CTG TTT ATC CGA CAT AAT
Ser Ala Ala Thr Thr Ala Ile Leu Ile Ala Arg Ser Asp Arg Pro Phe Leu Phe Ile Val Asp Pro Phe Leu Phe Ile Arg His Asn
        340                             350                             360

CCT ACA-GGT GCT GTG TTA TTC ATG GGG CAG ATA AAC CCC TGA AGAGTATACAAAAGAACCATGCAAAGCAACTGATGCAACTGTTCCTGTCTGGGAGGTATTGGAGGGAAAAAACA
Pro Thr Gly Ala Val Leu Phe Met Gly Gln Ile Asn Lys Pro ---
    370                         378

TTCCTGCATCTTTCTGTTAAATATCTTGTACATCGCATTCTTTTCAAAACGTAGTTTCTTAGGAAGCAGACTCGATGCAACTGTTCCTGTCTGGGAGGTATTGGAGGGAAAAAACA

AGCAGGATGCCTGGCACAGCTGTACTGAGGATTGATATAGAAAGACTTCCAGATGCCTAAAAGATTCTTTAAACTACTGACTGTTACCTAGGTTAACATCCCTGTTGAGGTATTTGCT

GTTGTCCAGTTAGGAATTTTTGTTTTGCTCTATATGTGCCGCTTTCAGAGAAGAAATTTAATCAGTGTGACAGAAAAAAAATGTTTATGGTAGCTTTTACTTTTTATGAAA

AAAAATTATTGTCCTTTAAATTCTTTCCCCATCCTTGATAGCAAGCGTTATTTGGGGTAGAAACGGTGAAATCTAGCCTCTTGTTTTGTTTGTGTT

GTTGTTGTTGTTTATATAATGCATGTATTCACTAAAATAAAACGTCCTGCTCTTGCTAGACAAGGTTGTGCATGTGCCTGTCACTACTGAGTCTGTGTCTACCTATGGA

TTTGCATTTTTGTATTTTGTACAAAGTAAAAATAACT
```

FIG. 1-2

SEQUENCE OF PROTEASE NEXIN I TYPE BETA

```
CTGTGACCCTCCTCGCCGCGCGCTTCGCTCGCTCCGACTCCCGCCGAGACTAGGCTCCGGTTGCGGGACCCCTCCGGCGCCCCTGGGGATCCAGGGAGCG

CGGTCGCTCCTTGGTGGAAGGAACC
                              S1                              S10                                          1
                          ATG AAC TGG CAT CTC CCC CTC TTC CTC TTG GCC TCT GTG ACG CTG CCT ATC TGC TCC CAC TTC AAT
                          Met Asn Trp His Leu Pro Leu Phe Leu Leu Ala Ser Val Thr Leu Pro Ile Cys Ser His Phe Asn
                           10                             20                            30
CCT CTG TCT CTC GAG GAA CTA GGC TCC AAC ACG GGG ATC CAG GTT TTC AAT CAG ATT GTG AAG TCG AGG CCT CAT GAC AAC ATC GTG ATC
Pro Leu Ser Leu Glu Glu Leu Gly Ser Asn Thr Gly Ile Gln Val Phe Asn Gln Ile Val Lys Ser Arg Pro His Asp Asn Ile Val Ile
          40                            50                            60
TCT CCC CAT GGG ATT GCG TCG GTC CTG GGG ATG CTT CAG CTG GGG GAC GCG GGG AGG ACC AAG CAG CTC GCC ATG GTG ATG AGA TAC
Ser Pro His Gly Ile Ala Ser Val Leu Gly Met Leu Gln Leu Gly Asp Ala Gly Arg Thr Lys Gln Leu Ala Met Val Met Arg Tyr
          70                            80                            90
GGC GTA AAT GGA GTT GGT AAA ATA TTA AAG AAG ATC AAC AAG GCC ATC GTC TCC AAG AAG AAT AAA GAC GTG GCT AAC GCC
Gly Val Asn Gly Val Gly Lys Ile Leu Lys Lys Ile Asn Lys Ala Ile Val Ser Lys Lys Asn Lys Asp Val Ala Asn Ala
          100                           110                           120
GTG TTT GTT AAG AAT GCC TCT GAA ATT GAA GTG CCT TTT GTT ACA AGG AAC AAA GAT GTG TTC CAG GTC AAT GTG AAC TTT
Val Phe Val Lys Asn Ala Ser Glu Ile Glu Val Pro Phe Val Thr Arg Asn Lys Asp Val Phe Gln Val Asn Val Asn Phe
          130                           140                           150                                    BglII
GAG GAT GCC GCC TCT GCC TGT GAT TCC ATC AAT GCA TGG GTT AAA GAA AAT ACC AGG GAT ATT GAC ATG CTG TCC CCA GAT CTT
Glu Asp Ala Ala Ser Ala Cys Asp Ser Ile Asn Ala Trp Val Lys Glu Asn Thr Arg Asp Ile Asp Met Leu Ser Pro Asp Leu
          160                           170                           180
ATT GAT GGT GTG CTC AGA ACC CTC GTC GTC AAC GCA GTG TAT TTC AAG GGT CTG TGG AAA TCA CGG TTC CAA GAG CCC GAG AAC ACA AAG
Ile Asp Gly Val Leu Arg Thr Leu Val Val Asn Ala Val Tyr Phe Lys Gly Leu Trp Lys Ser Arg Phe Gln Glu Pro Glu Asn Thr Lys
          190                           200                           210              SalI
AAA CGC GCA GCA GCC GAC GGG CCA GTG ATG TAT CAA GGG CTG GCC CAG CTC TCC GTG TTC CGG TGT GGG TCG ACA AGT GCC
Lys Arg Ala Ala Ala Asp Gly Pro Val Met Tyr Gln Gly Leu Ala Gln Leu Ser Val Phe Arg Cys Gly Ser Thr Ser Ala
          220                           230                           240               SacI
CCC AAT GAT TTA TGG TAC AAC TTC ATT GAA CCC CCA TAC CAC CTG GAA AGC ATC ATG ATT GCA CTG CCG ACT GAG AGC TCC ACT
Pro Asn Asp Leu Trp Tyr Asn Phe Ile Glu Pro Pro Tyr His Leu Glu Ser Ile Met Ile Ala Leu Pro Thr Glu Ser Ser Thr
```

FIG. 2-1

```
CCG CTG TCT GCC ATC ATC CCA CAC ATC AGC ACC AAG ACC ATA GAC TGG ATG AGC ATC ATG GTG CCC AAG AGG GTG CAG GTG ATC CTG
Pro Leu Ser Ala Ile Ile Pro His Ile Ser Thr Lys Thr Ile Asp Trp Met Ser Ile Met Val Pro Lys Arg Val Gln Val Ile Leu
    250                                                     260                                     270
CCC AAG TTC ACA GCT GTA GCA CAA ACA GAT TTG AAG GAG CCG CTG GAT ATT ACT GAC ATG TTT GAT TCA TCA AAG GCA AAT
Pro Lys Phe Thr Ala Val Ala Gln Thr Asp Leu Lys Glu Pro Leu Asp Ile Thr Asp Met Phe Asp Ser Ser Lys Ala Asn
        280                                     290                                     300
                                                                                                            HindIII
TTT GCA AAA ATA ACA GGG TCA GAA AAC CTC CAT GTT TCT CAT ATC TTG CAA AAA GCA AAA ATT GAA GTC AGT GAA GAT GGA ACC AAA
Phe Ala Lys Ile Thr Gly Ser Glu Asn Leu His Val Ser His Ile Leu Gln Lys Ala Lys Ile Glu Val Ser Glu Asp Gly Thr Lys
        310                                     320                                     330
GCT TCA GCA GCA ACA ACT GCA ATT CTC ATT GCA ACA TCA TCG CCT TGG TTT ATA GTA GAC AGA CCT TTT CTG TTT TTC ATC CGA CAT
Ala Ser Ala Ala Thr Thr Ala Ile Leu Ile Ala Thr Ser Ser Pro Trp Phe Ile Val Asp Arg Pro Phe Leu Phe Ile Arg His
        340                                     350                                     360
                                            378
AAT CCT ACA GGT GCT GTG TTA TTC ATG GGG CAG ATA AAC CCC TGA AGAGTATACAAAAGAACCATGCAAAGCAACGACTACTTTGCTACGAAGAAGACT
Asn Pro Thr Gly Ala Val Leu Phe Met Gly Gln Ile Asn Lys Pro
        370
CCTTCCGCATCTTTCTGTTAAATATTCTTGTACATCGCATTCTTTTTCAAAACGTAGTTTCTTAGGAAGCAGACTCGATGCAACTGTTCCTGTTCTGGGAGGTATTGGAGGGAAAAA
ACAAGCAGGATGCCTAGCACAGCTGTGACTGAGGATTGATATAGAAAGACTTCCAGATGCCTAAAGATTCTTAAACTACTGACTGTTACCTAGGTTAACATCCCTGTTGAGGTATTT
GCTGTTGTCCAGTTAGGAATTTTGTTTTTTATGCTCTATATGTGACAGAAAAAAAAATGTTTATGGTAGCTTTTACTTTTTATG
AAAAAAAATTATTTGTTCCTTTTAAATTCTTTCCCCATCCCCCCTCCAAAGTCTTGATAGCAAGCGTTATTTGCTAGACAAGGTTGCATGCCTGTCACTACTGAGTCTGTCTACCTAT
GTTGTTGTTGTTGTTTGTATTTTGTACAAGTAAAAATAACT
GGATTTGCATTTTTGTATTTTGTACAAGTAAAAATAACT
```

FIG. 2-2

USE OF PROTEASE NEXIN-I TO MEDIATE WOUND HEALING

CROSS-REFERENCE TO RELATED APPLICATIONS

This application is a continuation-in-part of pending U.S. patent application Ser. No. 025,450 filed Mar. 13, 1987; which is a continuation-in-part of now abandoned U.S. patent application Ser. No. 871,501 filed Jun. 6, 1986; which is a continuation-in-part of now abandoned U.S. patent application Ser. No. 870,232 filed Jun. 3, 1986; each of the above-referred-to applications is incorporated herein by reference in their entirety and priority under 35 USC Section 120 is claimed with respect to each of these applications.

FIELD OF THE INVENTION

This invention relates generally to the field of wound healing methods and to compositions and dressings useful in carrying out such methods. More specifically, this invention relates to using protease nexin-I (PN-I) to promote wound healing and to compositions and dressing which include (PN-I) and are useful in carrying out the wound healing methodology.

BACKGROUND OF THE INVENTION

Wound healing has three distinct phases: (1) inflammation; (2) cell migration and proliferation; and (3) remodeling. In the inflammatory phase, the wound is described by proteases released by inflammatory cells. Various lymphokines are secreted from neutrophils and macrophages that modulate the next phase of the wound healing. The second phase includes fibroblast migration, proliferation and the synthesis of new extracellular matrix molecules. These events appear to occur in a definite order where extracellular matrix molecules including fibronectin, collagen, and proteoglycans are secreted into the granulation bed. The first phase peaks at 3 days. The second phase of wound healing normally peaks at approximately one to two weeks after injury and is followed by a much longer third phase of tissue remodeling that begins within weeks and may last several months. During the remodeling phase, the connective tissue matrix matures as the disorganized collagen fibers are replaced by much thicker, more aligned collagen molecules. This tissue remodeling eventually contributes to the tensile strength of the wound and is sometimes accompanied by scar formation.

Connective tissue cells secrete protease inhibitors which are specific for serine proteases. Since serineproteases are involved in development and migration of cells, regulation of the activity of these enzymes is necessary to exercise control over the remodeling or destruction of tissues (*Proteases in Biological Control* (1975), Reich, E., et al., eds., Cold Spring Harbor, N.Y.). The inhibitors designated protease nexins irreversibly bind to serine proteases at their catalytic sites (Baker, J. B., et al., *Cell* (1980) 21:37–45) and effect the clearance of the bound proteases via receptor-mediated endocytosis and lysosomal degradation (Low, D. A., et al., *Proc Natl Acad Sci* (USA) (1981) 78:2340–2344; Baker, J. B., et al., in *The Receptors* 3 (1985), Conn, P. M., ed, Academic Press, in press).

Three protease nexins have been identified. Protease nexin-I (PN-I) has been purified from serum-free medium conditioned by human foreskin cells (Scott, R. W., et al., *J Biol Chem* (1983) 58:1043910444). Protease nexin-I is a 43 kD glycoprotein which is released by fibroblasts, myotubes, heart muscle cells, and vascular smooth muscle cells. Its release, along with that of plasminogen activator, is stimulated by phorbol esters and by mitogens (Eaton, D. L., et al., *J Cell Biol* (1983) 123:128). Native PN-I is an approximately 400 amino acid protein containing about 10% carbohydrate. Since it is present only in trace levels in serum, it apparently functions at or near the surfaces of interstitial cells. PN-1 inhibits all the known activators of urokinase proenzyme, plasmin, trypsin, thrombin, and factor Xa (Eaton, D. L., et al., *J Biol Chem* (1984) 259:6241). It also inhibits tissue plasminogen activator and urokinase.

A protein called neurite-promoting factor (NPF) has also been reported to be isolated from glioma cells, to have a 43 kD molecular weight, and to inhibit proteolysis catalyzed by urokinase or plasminogen activator (Guenther, J., et al., *EMBO Journal* (1985) 4:1963–1966). It was first reported as inducing neurite outgrowth in neuroblastoma cells (Barde, Y. A., et al., *Nature* (1978) 274:818). The amino acid sequence of this protein, but not the sequence of the cDNA encoding it, is disclosed in Gloor, S., et al., *Cell* (1986) 47:687–693. The NPF protein is a 379 amino acid sequence preceded by an 18 amino acid, met-preceded signal and is identical to PN-I.

Protease nexin-I is a serine protease inhibitor member of the serpin super family which is synthesized and secreted by cultured human fibroblasts. The protein represents about 1% of the secreted proteins of fibroblast and has a molecular weight of 43 kD. It reacts rapidly with trypsin, thrombin, urokinase and plasmin to inhibit these serine proteases. It does not react with chymotrypsin like proteases or PMN elastase. The protein has a high affinity for heparin and heparan-sulfate and can be readily purified by heparin affinity chromatography. Its close association with heparin indicates that it may be an extracellular matrix proteins surrounding fibroblasts. Recently, protease nexin has been shown to be identical with glia derived neurite promoting factor and is 30% homologous with antithrombin III.

The mitogenic activity of thrombin is effective only when added to cultures at concentrations above the concentrations of secreted PN-I (Baker, J. B., et al., *J Cell Physiol* (1982) 112:291; Low, D. A., et al., *Nature* (1982) 298: 2476). Thrombin is also known to cleave and inactivate acidic fibroblast growth factor Lobb, R. R., *Biochemistry* 27:2572–2578. It has been suggested that PN-I has an antiinflammatory function, since PN-I secretion by synovial fibroblasts increases dramatically when the cells are treated with interleukin-I (Krane, S., *Arth Rheum* 27:S24). PN-I may also have a neurological function, since the above-mentioned identical protease inhibitor stimulates neurite extension (Monard et al., *Prog Brain Res* (1983) 58:359).

Protease nexin has been reported to have several unique biological properties including the promotion of neural outgrowth in addition to endothelial cell migration and in addition of the inhibition of matrix destruction by fibrosarcomas. The specific role of serine proteases in these processes is not known. However, protease nexin was found to have an effect on the extracellular matrix of fibroblasts in culture. In connection with the conception of the present invention, we hypothesized that the use of protease nexin in several systems might help to elucidate roles of serine proteases in several cellular processes including cell migration, differentiation, and tissue remodeling. In order to obtain the present invention, we tested our hypothesis that protease nexin may play a role in promoting wound healing.

SUMMARY OF THE INVENTION

Large quantities of highly pure protease nexin-I (hereinafter PN-I) can now be obtained by the use of recombinant DNA technology as disclosed in our earlier filed U.S. patent application Ser. No. 025,450 to which we claim priority. The present invention provides a method of promoting wound healing by applying PN-I to a wound. Pharmaceutical compositions comprised of carriers having PN-I dispersed uniformly therein are disclosed as are such compositions further comprising antibiotics. A variety of wound dressings are taught which are comprised of a support surface having an absorbent material thereon surrounded by a pressure-sensitive adhesive strip. In some cases, the wound bed is kept moist with an occlusive dressing. The PN-I is present on the absorbent material, by itself, or in combination with other excipients or active components such as antibiotics or other macro molecules such as collagen, proteoglycan or heparin.

A primary object of the invention is to provide a method for increasing the rate of wound healing by the application of PN-I.

Another important object is to provide a pharmaceutical composition for topical application which is comprised of PN-I dispersed uniformly throughout a carrier with acceptable pharmacological properties.

Another object is to use PN-I in combination with other wound healing factors such as fibroblast growth factor, transforming growth factor beta or other bioactive molecules which aid in wound healing.

Yet another important object is to provide a wound dressing comprised of a support base having PN-I thereon.

An advantage of the present invention is that the method of applying PN-I to a wound facilitates the return of normal tissues.

A feature of the present invention is that the PN-I can be incorporated into a wide variety of different topical pharmaceutical compositions or placed on a variety of wound dressings to obtain the desired results of enhancing wound healing.

Another object is to prevent the degradation of other wound healing agents such as growth factors, collagen, fibronectin and other extracellular matrix molecules so as to promote healing.

Another object is to lengthen the lifespan of collagen implants for cosmetic and therapeutic treatments.

Another advantage results from the cotreatment of wounds with PN-I and growth factors wherein PN-I extends the half-life of the growth factors in the wound bed by preventing proteolytic degradation.

These and other objects, advantages and features of the present invention will become apparent to those persons skilled in the art upon reading the details of the structure, manufacture and usage as more fully set forth below, reference being made to the accompanying drawings forming a part hereof.

BRIEF DESCRIPTION OF THE DRAWINGS

FIG. 1 shows the nucleotide sequence of the coding region of PN-18 and the deduced amino acid sequence of PN-I alpha.

FIG. 2 shows the nucleotide sequence of the coding region of PN-33 and the deduced amino acid sequence of PN-I beta.

DEFINITIONS

Figure 3:
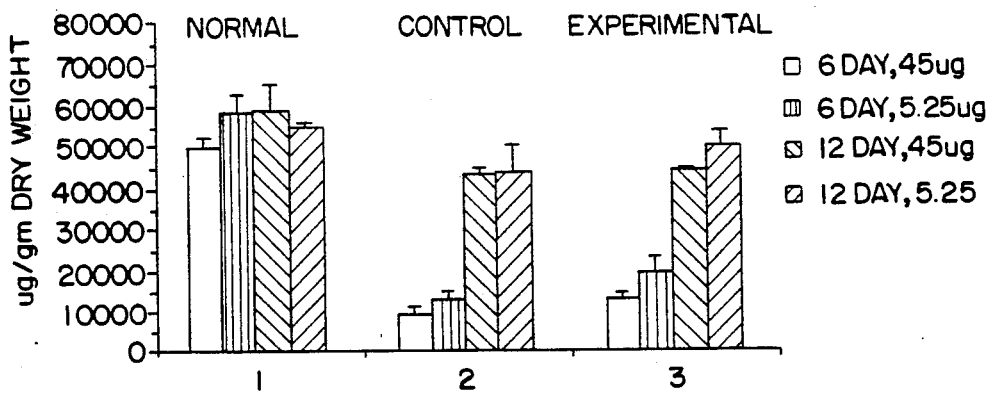
FIG. 3 is a graph showing the hydroxyproline content per dry weight of skin in a full thickness wound.

In describing the present invention, the following terminology will be used in accordance with the definitions set out below.

Herein the terms "protease nexin-I" (PN-I) and protease nexin shall be synonymous and shall refer to a protein which is active in the standard diagnostic assays for PN-I, which are based on four criteria, as follows: (1) The protein complexes to thrombin; (2) this complexation is accelerated by heparin; (3) the protein complexed to thrombin binds to fibroblasts; and (4) heparin inhibits this binding. PN-I is distinguishable from the two other protease nexin factors, PN-II and PN-III (Knauer, D. J., et al., *J Biol Chem* (1982) 257:15098–15104).

Recombinant PN-I was purified to homogeneity from serum-free medium conditioned by Chinese hamster ovary cells. Recombinant cells for producing PN-I are cultured under conditions suitable for the host in question, and the protein is recovered from the cellular lysate or from the medium, as determined by mode of expression. Purification of the protein can be achieved using methods similar to that disclosed by Scott, R. W., et al., *J Biol Chem* (1985) 260:7029–7034, incorporated herein by reference. The purified material shows the properties exhibited by PN-I when contained in conditioned medium, including formation of sodium dodecylsulfate-stable complexes with thrombin, urokinase, and plasmin; inhibition of protease activity; and heparin-enhanced inhibition of thrombin. The N-terminal amino acid sequence of the isolated, purified protease nexin was determined for the first 34 amino acids to be: Ser-His-Phe-Asn-Pro-Leu-Ser-Leu-Glu-Glu-Leu-Gly-Ser-Asn-Thr-Gly-Ile-Gln-Val-Phe-Asn-Gln-Ile-Val-Lys-Ser-Arg-Pro-His-Asp-Asn-Ile-Val-Ile.

"Compositions" or "formulations" of the invention refer to any mixture containing the purified PN-I which protein is formulated according to its pharmaceutical applications for wound healing. The protein is formulated into compositions using pharmaceutically acceptable excipients, as is understood by practitioners of the art, and disclosed, for example, in *Remington's Pharmaceutical Sciences*, latest edition, Mack Publishing Company, Easton, Pa.

There are two forms of PN-I, PN-I alpha and PN-I beta. They are highly homologous and contain 378 and 379 amino acids, respectively in the mature sequence, differing only at position 310 where the Arg of PN-I alpha is replaced by Thr-Gly in PN-I beta. Both have a 19 amino acid signal beginning at Met. The location of the N-terminus is deduced from the sequenced native protein and it is highly likely this is correct; however, there is a small probability that alternate processing site(s) may also be utilized.

"Purified" or "pure" refers to material which is free from substances which normally accompany it as found in its native state. Thus "pure" PN-I-encoding DNA refers to DNA which is found in isolation from its native environment and free of association with DNAs encoding other proteins normally produced by cells natively producing PN-I. "Pure" PN-I refers to PN-I which does not contain materials normally associated with its in situ environment in human or other mammalian tissue. Of course, "pure" PN-I may include materials in covalent association with it, such as glycoside residues or materials introduced, for example, for formulation as a therapeutic. "Pure" simply designates a situation wherein the substance referred to is, or has been, isolated from its native environment and materials which normally accompany it.

DETAILED DESCRIPTION AND PREFERRED EMBODIMENTS

Before the method of enhancing wound healing and compositions and dressings containing PN-I and processes for making and using such are disclosed and described, it is to be understood that this invention is not limited to the particular formulations, processes or methods of use described as such compositions, dressings and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a pharmaceutically acceptable carrier or excipient" includes mixtures of carriers or excipients, references to "an antibiotic" include reference to mixtures of such antibiotics, reference to "the method of administration or use" includes one or more different methods of administration or use known to those skilled in the art.

The essence of the present invention is somewhat straight forward in that it involves the application of PN-I to a wound on a living mammal in order to promote an increased rate of healing of the wound as compared to the same wound which does not have a PN-I thereon. Because PN-I is somewhat expensive and need not be applied in a highly concentrated form, it is generally formulated in a pharmaceutical composition by dispersing PN-I in a carrier. PN-I is also readily bound to extracellular matrix molecules, one may be applied as a dilute solution to the wound bed followed by allowing the liquid to absorb into the wound bed.

In general, PN-I is not applied in a pure form to a wound, but is formulated in combination with one or more excipients and/or other active ingredients such as collagen, proteoglycan, heparin, heparin sulfate, gelatin, hyaluronic acid, lamin, fibronectin or fibrin. The PN-I is generally present in the formulation as a minor ingredient i.e., less than 50% and more generally about 0.01% to 1% PN-I by weight and more preferably about 0.05 to 0.5% by weight PN-I.

The amount of the PN-I needed in order to obtain an improvement in the rate of wound healing, varies depending on the particular type of wound and the particular individual. Further, the number of applications and the period of time over which the applications are made can vary considerably depending on factors such as the type of wound, size of wound, age and size of the patient and general health of the patient. The precise amounts, numbers and periods of administration can be determined by the health care provider. As a guide line, a composition comprised of 0.01 to 1.0 weight percent of PN-I and 99.99 to 99.0 weight percent of excipient can be applied to a wound on a daily basis over a period of one month. The composition is applied in an amount of about 0.01 to 20 grams per square centimeter of wound surface and the wound should be cleaned as needed.

The protease nexin-I of the invention is preferably formulated in a semisolid cream or ointment like or more preferably gel formulation. However, the formulation may be in the form of a solution having the protease nexin-I therein. The protease nexin-I solution may be applied to a full thickness wound after the wound is cleaned and the surface of the wound is allowed to dry slightly after which there is applied about 0.1–100 ug per square centimeter of wound. However, the type of formulation and amount of protease nexin-I applied will be determined to a large extent by the care giver treating the wound. In certain instances, as much as 1 mg of protease-nexin I may be applied per square centimeter of wound. When applying the protease-nexin I in any form, it is important to first clean the wound and remove any wound fluid that may limit the protease nexin-I from absorbing to the granulation tissue in the wound bed. Although a single application of protease nexin-I is effective, in order to obtain the best results, it may be necessary for the protease nexin-I to be applied periodically, such as every day, or every other day depending on the individual, the type of wound and the stage of the wound healing. Again, the amount of protease nexin-I and the frequency at which it is applied, is a matter which can readily determined by the care giver. In the specific example described herein, a protease nexin-I solution was applied in an amount of about 5–45 mg per 4 square centimeters of wound and improved wound healing results were observed as compared with a wound not treated with protease nexin-I.

In order to test the direct effect of the PN-I on wound healing, different tests were carried out as described further below. However, it is important to note that one important test involves the determination of the hydroxyproline content of the wound as it continues to heal. The hydroxyproline content is an estimation of the collagen content of the wound. As the collagen content of the wound increases, the wound is further healed and regains strength. Accordingly, when carrying out tests with the present invention, the PN-I was not used in combination with collagen as such a combination would potentially affect the results obtained by potential contamination of the wound material being tested with collagen from the composition being applied. However, it is recognized that collagen compositions represent state of the art methods of treating various types of wounds and specifically large burn wounds. Accordingly, a preferred embodiment of the invention involves dispersing PN-I in collagen or a collagen-based dressing which is then applied to a wound surface. In order to more particularly point out and distinctly describe the invention, methods of obtaining collagen and terminology describing the type of collagen which might be useful in connection with the present invention is given below.

In general, the collagen is present as the excipient in amount ranges as indicated above. The PN-I could be used in a higher concentration with collagen, e.g., 1.0–10.0% PN-I with 99.0 to 90.0% collagen.

Collagen as an Excipient

A preferred embodiment of the present invention involves the use of collagen material. Initially, the collagen is obtained from a natural source. However, the collagen used in connection with the present invention is not "native" or "natural" collagen. It has been modified to some extent in order to purify the collagen material and change its structure in an attempt to eliminate the generation of an immune response when the collagen comes into contact with living tissue. Such collagen is generally referred to as "pharmaceutical grade collagen". A general description of collagen and how "native" or "natural" collagen is modified to obtain a pharmaceutical grade collagen is put forth below.

Native collagen consists in large part of a triple helical structure containing repeating triplet sequences composed of glycine linked to two additional amino acids, commonly proline and hydroxyproline; thus, glycine appears in every third position in the chain. In addition, all collagen chains contain regions at each end which do not have the triplet glycine sequence and are thus not helical. These regions are thought to be responsible for the immunogenicity associated with most collagen preparations. Immunogenicity can, in large part, be mitigated by removal of these regions to produce "atelopeptide" collagen. This can be accomplished by digestion with proteolytic enzymes such as trypsin, chymotrypsin, papain, or pepsin. Because of differing specificities of these proteases, the degree of completeness of removal of the telopeptides varies. Thus certain proteases, which effect the most complete removal, are preferred. Included among these is trypsin, which results in removal of substantially all of the telopeptide portions.

The nonhelical telopeptide regions are also responsible for forming the cross-links which aid in stability of the fibrillar structure. These regions contain aldehydes capable of cross-linkage to lysine residues. Atelopeptide collagen must be cross-linked artificially, if it is so desired.

While all collagens share the foregoing characteristics, they have been subclassified into approximately twelve types depending on the precise amino acid sequence in the individual chains of the triple helix, the carbohydrate content, and the presence or absence of disulfide cross-linking. The most common subtypes are Type I which is present in skin, tendon, and bone, and which is made by fibroblasts, and Type III which is found primarily in skin and is associated with Type I. Other types reside in specialized membranes, cartilage, or at cell surfaces. Types I and III contain similar numbers of amino acids in their helices; however, Type III (but not Type I) contains two adjacent cysteines at the C-terminal ends of the triple helix which are capable of forming interchain cross-links.

Type I collagen contains one alpha 2 (I) and two alpha 1 (I) chains each of which contains 1014 amino acids in its triplet region; there are several carbohydrate moieties present on each chain. Type III collagen contains only alpha 1 (III) (3 chains) which contain 1026 residues in their triplet regions. As stated above, the presence in Type III of a pair of adjacent cysteine residues at the carboxy terminal end of the triplet region results in stability of the interchain cross-links. Both collagens contain short nontriplet ends (telopeptides). The reconstituted fibrillar atelopeptide skin collagen used in this invention contains the atelopeptide forms of both Type I and Type III; the bone collagen powder consists of the atelopeptide form of Type I exclusively.

A pharmaceutical grade collagen material sold under the tradename "Zyderm" (sold by the Collagen Corporation of Palo Alto, Calif.) can be used in connection with this invention.

Experimental Testing

Recombinant PN-I was tested on guinea pig full thickness accession wound model. Guinea pigs were given two 2×2 centimeter wounds on the sides of their backs equidistant from the midline. The wounds were bandaged for 24 hours using a Bioclusive dressing. At 24 hours, the guinea pigs were given a dose of 5.25 or 45 micrograms PN-I in a volume of 300 microliters onto one wound bed. The second wound on the same animal served as control. The guinea pigs were allowed to heal for either six or 12 days after which time the wound was evaluated by determining the hydroxyproline per dry weight, the hydroxyproline per DNA and the tensile-strength of the excised wounds. The results of these evaluations are shown respectively in FIGS. 3, 4 and 5.

The wound beds were removed, fixed in Bouin's fixative, embedded in paraffin sections at 5 um, and stained with Mason's Trichrome stain for histological examination. Comparing the experimental and control wounds, the results indicated that in six days the hydroxyproline per gram dry weight was increased significantly from $9.42 \pm 2.3$ to $13.13 \pm 1.6$ mg per gram. Hydroxyproline per DNA increased from $3.14 \pm 0.88$ to $4.6 \pm 0.62$ micrograms per microgram; however, the modulus of the stress-strain curves was not different. After 12 days, the hydroxyproline per gram dry weight and the hydroxyproline per DNA of PN-I treated wound were unchanged compared to the controls, however, the modulus of the stress-strain curve was increased from $0.64 \pm 0.156$ MPa to $1.24 \pm 0.22$ MPa.

Histological analysis of the Mason's Trichrome stained wound beds indicated that the granulating bed of wounds treated with protease nexin were more active than control wounds both at 6 days and 12 days and there was a significantly larger increase in the number of new blood vessel formation on the PN-I treated wounds. The results indicated that a single dose of PN-I applied to full thickness dermal wound (at the on site of granulation formation) improves matrix formation in six days and increased wound strength by 12 days. Furthermore, the results indicate that protease nexin-I appears to stimulate new vessel formation and may be angiogenic in full thickness wounds.

EXAMPLE 1

We chose to use the full thickness dermal wound model in guinea pigs because this model provides a relatively large granulation bed in which the early phases of wound healing can be studied and quantified.

Female Hartley Albino guinea pigs weighing 400 grams were obtained from Hilltop Breeders, maintained in a vivarium and fed guinea pig chow and water ad. lib. for one week to insure that they were healthy. On the day prior to surgery, the backs of the guinea pigs were shaved and depilated. On the day of surgery, two full thickness 2×2 centimeter wounds were prepared on either side of the middle of the back. The normal skin, excised to the level of the panniculus carnosus, was reserved for data analysis. The wounds were lavaged with 0.3 ml penicillin/streptomycin, Gibco Co., at a concentration of 100 units per ml and bandaged with "Bioclusive" transparent dressing. Twenty-four hours after surgery, the wound beds were uninfected and dry. The surface of the "Bioclusive" dressing was swabbed with an alcohol wipe, 0.3 ml sterile solution of 20 mM sodium citrate, 300 mM sodium chloride buffer pH 7.2 was injected through the dressing onto the control wound site. The experimental site received 0.3 ml of sterile buffer containing a dose of protease nexin. After absorption, the dressing was removed, the wound bed treated with a triple antibiotic ointment containing Bacitracin, Heomycin and Polymyxin B and rebandaged with a Bioclusive dressing. At the termination of the experiment, strips of skin 0.5 cm × 3 cm × 10 cm were dissected so that the wound bed was in the center of the strip. A strip of normal skin was also excised. The strips were tested for tensile strength using an Instron mechanical tester. Two quadrants of the wound bed including peripheral normal skin were removed for histology. Two quadrants of the wound were removed for analysis of hydroxyproline and DNA content.

Mechanical Testing

In order to determine whether or not protease nexin influenced the wound strength, normal skin, experimental and control wounds were tested for tensile strength. Rectangular strips of tissue were removed from the wound so that the wound bed was centered between two pieces of normal tissue. These tissue strips were placed in an Instron tester and subjected to a constant strain rate of 10%; the tress was measured as a function of strain.

Collagen and DNA Analysis

Two quadrants of the granulation bed of the control and experimental wounds were lyophilized to dryness. The dry weight was determined. For hydroxyproline determination, the sample for hydroxyproline determination was hydrolyzed in 6 NHCl for 48 hours, and the hydroxyproline content was determined using a chemical assay for hydroxyproline, see Methods in Enzymology, Vol. 82 "Structural and Contractible Proteins" Academic Press, N.Y. 1982, see page 372-399 by Richard A. Berg. Hydroxyproline was calculated as hydroxyproline per dry weight. Total DNA content of the other wound quadrant was determined by extraction with perchloric acid and reaction with diphenolamine as described by Dische and modified by Burton. DNA was calculated as micrograms DNA per gram dry weight. The values for hydroxyproline and DNA were combined in order to calculate the hydroxyproline per DNA. Hydroxyproline is an estimation of the collagen content of the wound. DNA is an estimation of the cellularity of the wound.

Light Microscopy and Histoloqy

Samples of tissue for light microscopy were fixed in Bouin's, embedded in paraffin and sectioned at 5 uM using a Sorval JB-4 microtome with a Lipshaw knife holder. Duplicate sections were stained in H&E Mason's Trichrome Picrosirius Red. Mason's Trichrome stained section were visualized using a microscope. Photographed Mason's Trichrome stains collagen, blue; muscle, red; keratin, yellow; and fibrin, red.

EXAMPLE 2

Angiogenesis

Light microscopy of cross-section of experimental wounds suggested that protease nexin enhanced angiogenesis of the granulation bed. To test this hypothesis, protease nexin was examined for angiogenic activity using an assay technique of assaying the chorioallantoic membrane as described in Thompson et al., *Journal of Pathology*, Vol. 145:27-37 (1985). Protease nexin was soaked into a three dimensional collagen sponge at various concentrations using a total of 0.1 ml per sponge diameter, 0.5 cm. 1 ml thick. The sponges containing the protease nexin were applied to the surface of the chorioallantoic membrane (CAM) of 10 day embryos. After 4 days, the CAMs were removed, fixed in formalin, examined by microscopy and quantitated by the method of Thompson et al cited supra.

To visualize vessel development in the guinea pig, tissue sections of the wound beds were oriented so that paraffin embedded tissues could be sectioned parallel to the skin surface. These sections were also stained with Mason's Trichrome stain. The number of vessels appearing in the granulation tissue could be quantified.

Collagen Synthesis

At six days, hydroxyproline synthesis per dry weight and per DNA and the control was increased in the experimentals vs. the controls. By 12 days, the hydroxyproline per gram dry weight and hydroxyproline per gram had reached levels that approached levels of normal skin. However, the strength of the wound at 12 days is much less than normal skin due to the much lower organization within the collagen fibrils in the wound bed. In this model, the strength of the wound is gained by reorganization through remodeling of the collagen fibers in the extracellular matrix that occurs between 3 weeks and 6 months. By 12 days, the difference in hydroxyproline between the experimental and the control was not as significant as it was in 6 days and contrast with the increase in wound strength with the control as determined by the mechanical properties of the wounds.

Mechanical Testing

In 6 days, the modulus of the stress stain curve was much lower than that of normal skin. However, the ultimate tensile strength was also much lower than normal skin and there was no significant difference between the protease nexin treated and control wounds. At 12 days post-wounding, there was an increase in modulus and ultimate tensile strength before the experimental wounds compared with the controls with an average increase of from 0.6±1.56 to 1.24±0.22. In this experimental model, the major increase of wound tensile strength does not begin to occur until 3 weeks post-wounding, the results indicate a difference between the experimental and the controls, which would be expected to be even greater with longer remodeling time.

Histological Analysis

Examination of sections of the 6 day wound beds stained with Mason's Trichrome indicated that the wound beds of the site treated with protease nexin had an increased cellularity, a more active granulation tissue, and a wider margin of hypertrophic cells at the edges of the wound than the control site. By 12 days, these differences were more pronounced and, in addition, the experimental wound bed appeared to contain increased numbers of blood vessels when compared with the control wound. During the final dissection of the wound beds, it was observed that the base of the wound site appeared to contain more blood vessels and was much more difficult to separate from the underlying muscle layer.

Results

Protease nexin has been observed to have a number of biological functions involving cell movement and the promotion of neural outgrowth by alterations of endothelial cell mobility. It has also been observed to affect the degradation of extracellular matrix. The results obtained with a single dose of protease nexin onto the granulation bed of full thickness dermal wounds on guinea pigs indicates that protease nexin has an affect of promoting wound healing as evidenced by an increase in wound strength and by an early increase in collagen synthesis as determined by hydroxyproline content of the granulation tissue. Histological analysis has showed that protease nexin affects the cellularity of the wound bed and appears to promote formation of new blood vessels.

In terms of the known effects of protease nexin, i.e., inhibition of thrombin and urokinase, it is possible that protease nexin affects wound healing by affecting the synthesis of matrix macromolecules present in the granulation bed.

Referring to FIG. 3, it is pointed out that at either 6 or 12 days post-wounding, the granulation bed was dissected from the animal, lyophilized, hydrolyzed and hydroxyproline content determined as described in Materials and Methods. Normal values are derived from normal skin, excised to create the full thickness wound. Control values were derived from wounds dosed with buffer only. Experimental values were derived from wound beds treated with protease nexin applied one day post-wounding.

Figure 4:
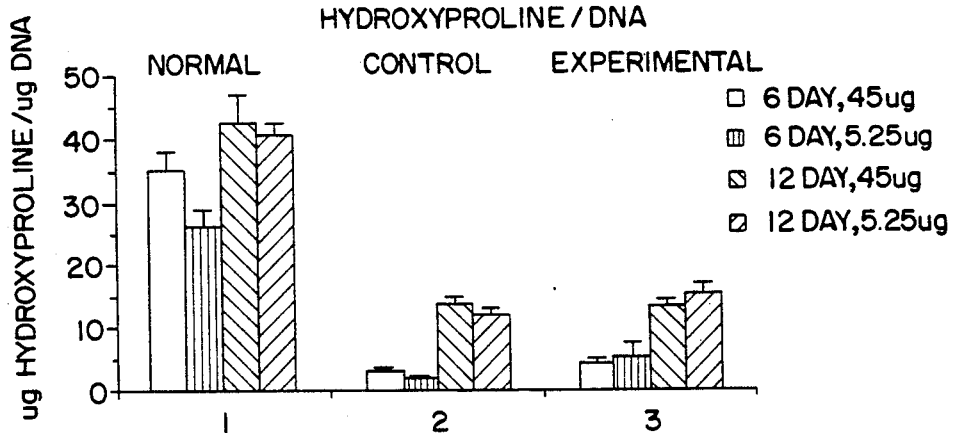
FIG. 4 is a graph showing the hydroxyproline content per DNA in a full thickness wound.

The results shown in FIG. 4 were obtained when the beds were dissected, lyophilized and weighed. The DNA was determined as described in Materials and Methods. Hydroxyproline values were determined as described above in connection with FIG. 3 and were corrected by the DNA content of the wound to obtain a hydroxyproline per DNA. Values for normal skin are derived from skin excised in the creation of the wound. Control values are derived healing the wound beds in the absence of protease nexin. Experimental values were derived from wound beds treated with a single dose of protease nexin.

Figure 5:
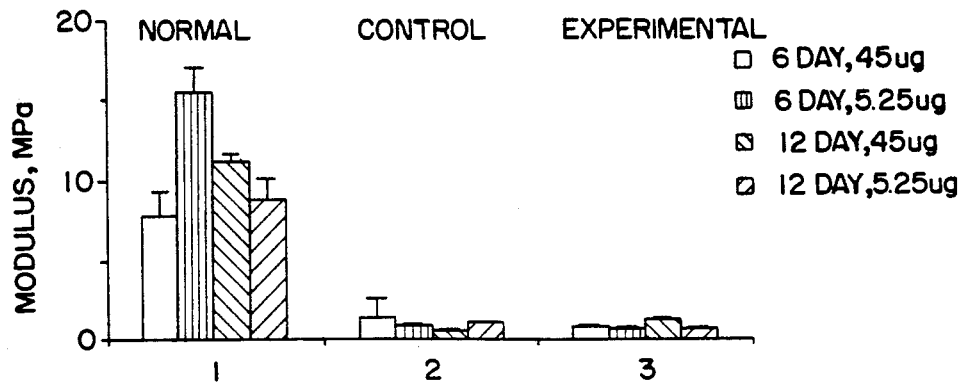
FIG. 5 is a graph showing the modulus of the stress strain curves in a full thickness wound.

In order to obtain the results shown in FIG. 5, stress strain curves were obtained for normal guinea pig skin and for both control wounds and wounds treated with protease nexin. The specimens were prepared as described above in the Materials and Methods section.

While the present method of enhancing wound healing, compositions and dressings for obtaining such have been described with reference to specific methodologies, compositions and dressings, it should be understood by those skilled in the art that various changes may be made and equivalence may be substituted without departing from the true spirit and scope of the invention. In addition, many modifications may be made to adapt to a particular type of wound, individual, excipient material or dressing in order to obtain the objective, spirit and scope of the present invention. All such modifications are intended to be within the scope of the claims appended hereto.

What is claimed is:

1. A method of treating a wound on a living mammal, comprising the steps of:
    applying a therapeutically effective amount of purified protease nexin-I locally to the area of the wound; and
    allowing the protease nexin-I to remain in contact with the wound for a sufficient period of time to allow for the protease nexin-I to promote healing of the wound.

2. The method as claimed in claim 1, wherein protease nexin-I is applied in combination with a pharmaceutically acceptable carrier.

3. The method as claimed in claim 1, wherein the protease nexin-I is periodically applied to the wound.

4. The method as claimed in claim 1, further comprising:
    covering the wound with an occlusive dressing.

5. The method as claimed in claim 1, further comprising periodically cleaning the wound and reapplying the protease nexin-I.

6. A pharmaceutical composition for wound healing, comprising:
    a carrier in the form of a collagen; and
    a therapeutically effective amount of purified protease nexin-I dispersed in the carrier.

7. The composition as claimed in claim 6, wherein the carrier is in the form of a collagen gel.

8. The composition as claimed in claim 6, wherein the protease nexin-I is present in amount in the range of 0.01 to 1.0 weight percent.

9. The composition as claimed in claim 8, wherein the protease nexin-I is present in an amount in the range of 0.05 to 0.5 weight percent.

10. The composition as claimed in claim 6, wherein the collagen is a pharmaceutically grade atelopeptide collagen.

11. The composition as claimed in claim 6, wherein the protease nexin-I is protease nexin-I $\alpha$.

12. The composition as claimed in claim 6, wherein the protease nexin-I is protease nexin-I $\beta$.

13. A pharmaceutical composition for wound healing, comprising:
    a carrier selected from the group consisting of proteoglycan, laminin, fibronectin, hyaluronic acid and gelatin; and
    a therapeutically effective amount of purified protease nexin-I dispersed in the carrier.

14. The composition as claimed in claim 13, wherein the protease nexin-I is present in an amount in the range of 0.01 to 1.0 percent.

15. The composition as claimed in claim 14, wherein the protease nexin-I is present in an amount in the range of 0.05 to 0.5 weight percent.

* * * * *